(12) United States Patent
Chinn et al.

(10) Patent No.: US 8,535,700 B2
(45) Date of Patent: Sep. 17, 2013

(54) PRO-FIBROTIC COATINGS

(75) Inventors: Joseph A. Chinn, Shakopee, MN (US); Stephen J. Chudzik, St. Paul, MN (US); Sean M. Stucke, Farmington, MN (US)

(73) Assignee: Surmodics, Inc., Eden Prairie, MN (US)

( * ) Notice: Subject to any disclaimer, the term of this patent is extended or adjusted under 35 U.S.C. 154(b) by 1497 days.

(21) Appl. No.: 11/261,954

(22) Filed: Oct. 28, 2005

(65) Prior Publication Data

US 2006/0105012 A1     May 18, 2006

Related U.S. Application Data

(60) Provisional application No. 60/623,565, filed on Oct. 28, 2004, provisional application No. 60/623,563, filed on Oct. 28, 2004.

(51) Int. Cl.
| | |
|---|---|
| *A61L 27/34* | (2006.01) |
| *A61L 31/10* | (2006.01) |
| *C08L 89/06* | (2006.01) |
| *A61F 13/00* | (2006.01) |
| *B05D 3/00* | (2006.01) |

(52) U.S. Cl.
USPC .......................................... 424/422; 427/2.26

(58) Field of Classification Search
None
See application file for complete search history.

(56) References Cited

U.S. PATENT DOCUMENTS

| | | | |
|---|---|---|---|
| 4,167,415 A * | 9/1979 | Higuchi et al. ............. 430/286.1 |
| 4,973,493 A * | 11/1990 | Guire ............................. 427/2.24 |
| 5,002,582 A | 3/1991 | Guire et al. |
| 5,328,955 A * | 7/1994 | Rhee et al. ..................... 525/54.1 |
| 5,330,911 A | 7/1994 | Hubbell et al. |
| 5,414,075 A | 5/1995 | Swan et al. |
| 5,637,460 A | 6/1997 | Swan et al. |
| 5,714,360 A | 2/1998 | Swan et al. |
| 5,874,500 A * | 2/1999 | Rhee et al. ..................... 525/54.1 |
| 5,900,245 A | 5/1999 | Sawhney et al. |
| 6,007,833 A | 12/1999 | Chudzik et al. |
| 6,156,345 A | 12/2000 | Chudzik et al. |
| 6,162,241 A | 12/2000 | Coury et al. |
| 6,254,634 B1 * | 7/2001 | Anderson et al. ............ 623/1.42 |
| 6,278,018 B1 | 8/2001 | Swan |
| 6,585,765 B1 * | 7/2003 | Hossainy et al. ............ 623/1.45 |
| 6,632,446 B1 | 10/2003 | Hubbell et al. |
| 7,009,034 B2 | 3/2006 | Pathak et al. |
| 2003/0165613 A1 | 9/2003 | Chappa |

FOREIGN PATENT DOCUMENTS

| | | |
|---|---|---|
| WO | WO 01/66161 | 9/2001 |
| WO | WO 02/13871 | 2/2002 |
| WO | WO 02/100453 | 12/2002 |
| WO | WO 03/097117 | 11/2003 |

OTHER PUBLICATIONS

International Search Report for International Patent Application No. PCT/US2006/038959, mailed on Apr. 10, 2006 (3 pgs).

* cited by examiner

*Primary Examiner* — Suzanne Ziska

(74) *Attorney, Agent, or Firm* — Kagan Binder, PLLC

(57) ABSTRACT

Pro-fibrotic coatings for medical articles are described that include a pro-fibrotic polymer such as collagen. The pro-fibrotic coatings can also include a thromboresistant polymer. The coatings can be formed by activation of photoreactive groups pendent or independent of the coating materials.

21 Claims, No Drawings

PRO-FIBROTIC COATINGS

CROSS-REFERENCE TO RELATED APPLICATIONS

The present non-provisional Application claims the benefit of commonly owned provisional Application having Ser. No. 60/623,565, filed on Oct. 28, 2004, and entitled PRO-FIBROTIC COATINGS; and commonly owned provisional Application having Ser. No. 60/623,563, filed on Oct. 28, 2004, and entitled PRO-FIBROTIC COATINGS WITH MODULATORS, which Applications are incorporated herein by reference in their entirety.

TECHNICAL FIELD

The present invention relates to methods for providing a pro-fibrotic coating to medical articles. Medical articles having a pro-fibrotic coating can be used to promote formation of a fibrotic clot useful for in vivo space-filling functions such as hemostasis and occlusion.

BACKGROUND

The process of surface coating implantable medical articles has proved to be valuable in cases where it is desired to provide the article surface with a property that is not present on the uncoated surface. For example, polymer compositions have been applied to medical devices to improve the wettability and lubricity of surfaces. Coatings can also provide features that improve the biological function of the article. In particular, bioactive agents can be presented on, or delivered from, the article surface to locally or systemically affect blood and vascular components thereby affecting bodily processes such as hemostasis and angiogenesis.

Surface coatings have also been used on implantable medical articles, such as fabrics, to promote a local response leading to thrombus formation. Thrombogenic materials present in surface coatings can provide a sealant function to a medical article, such as cardiac patch, which is typically constructed of porous materials. The sealant coating can promote a thrombogenic response at the coated surface. Factors involved in the thrombogenic response, such as cells involved in tissue repair and matrix factors such as fibrin, associate with the surface of the device and, over time, provide a sealant function to the surface. The thrombogenic response can lead to tissue in-growth in the pores of the device surface and the newly formed tissue can provide a sealant function.

Thrombogenic materials have also been used in connection with vascular occlusion devices such as occlusion coils, wires, or strings. These occlusion devices are typically delivered to a target site within a body lumen, such as an aneurysm, via a catheter. For example, an occlusion coil is advanced into the aneurysm until the coil occupies the aneurysm. These coils are intended to space-fill the aneurysm sac by the volume displaced by the coils themselves, or, if the coil is thrombogenic, in combination with the accumulation of biological material related to the induced thrombus formation in the vicinity of the coils.

Utilizing a thrombogenic coil can provide advantages for the treatment of vascular abnormalities such as aneurysms, but can also be challenging from various standpoints. For example, one challenge is to promote thrombus formation to space-fill the aneurysm without causing embolism, as a result of a portion of the clot dislodging from the aneurysm. In this case, thrombogenic coatings should ideally promote clot formation with reduced risk of embolism. More specifically, thrombogenic coatings should improve the rate and quality of clot maturation and subsequent formation of neointima and neoendothelial coverage near the neck of the aneurysm.

Occlusion coils prepared from uncoated platinum elicit little, if any, of a biological response and therefore are not ideal for promoting rapid thrombus formation in the aneurysm. In order to improve the thrombogenic response, platinum occlusion coils have been coated with collagen. However, the stability of the collagen coating on the coil was poor and the process of delivering the coil to the aneurysm compromised the coating. Therefore, prior art shows that coatings designed to elicit a thrombogenic response suffer from poor quality and therefore insufficient durability.

In addition to difficulties with immobilizing proteins (such as collagen) on these surfaces there are other drawbacks and concerns with using these types of coating materials, particularly animal-derived materials. For example, collagen and gelatin are commonly derived from animal sources and used in many coating applications where a thrombogenic response is desired. One problem associated with use of these materials is that it is difficult to produce consistent coating compositions from these animal sources due to batch-to-batch variations inherent in their production.

In many cases the collagen used in coating technologies is bovine derived. In these cases there is the possibility that bovine collagen preparations may contain unwanted contaminants that are undesirable for introduction into a human subject. One example of an unwanted contaminant is the prionic particles that cause Bovine Spongiform Encephalopathy (BSE).

BSE, also termed Mad Cow Disease, is one of a group of progressive neurological diseases called transmissible spongiform encephalopathies, or TSEs (named for deteriorated areas of the brain that look like sponges). Various forms of TSE have been reported, including scrapie in sheep and chronic wasting disease in elk and mule deer. It is generally believed that the use of recycled animal parts led to the cross-species contamination of scrapie in sheep to mad cow disease, and the ingestion of contaminated beef and bovine products led to the human variant of this disease, Creutzfeldt-Jakob Disease (CJD).

Additional concerns are that preparations from animal sources may provide other unwanted contaminants, such as antigenic factors. These antigenic factors may promote a localized immune response in the vicinity of the implanted article and foul its function. These factors may also cause infection as well as local inflammation.

Overall, the prior art show that coatings on devices that are used in the body to provide hemostatic and occlusion functions, wherein coating designed to elicit a thrombogenic response on the surface of the device, often suffer from poor quality. These coating are not suitable for promoting a local response leading to thrombus formation on the surface of the coated device.

SUMMARY OF THE INVENTION

The present invention provides compounds, compositions, and methods useful for preparing articles having pro-fibrotic coatings, as well as coated articles. The present invention also encompasses the use of articles having pro-fibrotic coatings, as described herein, for medical purposes.

Articles coated according to the invention can provide a rapid and localized fibrotic response leading to the accumulation of clotting factors and formation of a fibrin clot in the vicinity of the coated article. In some aspects, the pro-fibrotic coatings can be used to promote space filling in an area of the body in which the coated article has been delivered. The pro-fibrotic coatings can be formed on various medical articles. The coated medical articles can then be delivered to areas of the body where a hemostatic function is desired. In some aspects of the invention, the pro-fibrotic coatings are formed on the surface of vascular occlusion devices, such as vascular occlusion coils.

In another aspect of the invention, the pro-fibrotic coating is formed on an article having a porous surface. Particularly useful implantable articles having porous surfaces include fabrics such as surgical patches.

The coatings of the invention are directed at forming an organized fibrin clot and further directed at forming a clot that has a reduced likelihood of embolizing into the bloodstream. The clot associated with the coated surface can act as a hemostatic barrier, preventing, or at least reducing, the movement of body fluids such as blood into or through the clotted area.

The pro-fibrotic coatings of the present invention provide a number of distinct advantages when used in connection with implantable medical articles.

One advantage relates to improved quality and durability of the pro-fibrotic coatings. The present coatings can be formed on the surface of an article with no or insignificant surface defects. For example, surface imaging of the coatings revealed no cracking or delamination of the coating, which would otherwise lead to problems during use. Because the pro-fibrotic coatings of the invention are well formed, they demonstrate improved durability in use, and therefore provide additional safety to a patient.

Another advantage relates to the ability to control the thickness of the coating. This can be particularly useful for small implantable articles that have complex geometries or have surfaces that are otherwise difficult to coat. In some aspects, the coating can be less than 5 μm, such as about 2-3 μm. In other aspect, the coating can be thicker, such as greater than about 5 μm. A thicker coating can be useful when it is desired to perform a space filling function, such as with the treatment of aneurysms.

Another advantage relates to lubricity of the coated surfaces. In particular, the pro-fibrotic coatings can improve the lubricity on the surface of the coated article. This, in turn, can facilitate the movement of the coated article within a catheter and into a target site during a medical procedure. Articles coated with the pro-fibrotic coatings, such as wires, coils, and strings, can be delivered to a target site within the body, such as an aneurysm, with low frictional resistance.

The pro-fibrotic materials are also designed to form a stable coating on the surface of the device. The coatings are stable, at least initially, as the coated article is delivered to the target site within the body. In some cases the coating materials may be at least partially biodegradable and can erode from the surface.

In some aspect of the invention, photoreactive groups are utilized and allow the pro-fibrotic polymers to be covalently bound to the medical article, or to become stably associated with the medical article. This provides improved association of the pro-fibrotic polymer with the medical article. Processes such as delivery of the coated article to a target site will not significantly compromise the pro-fibrotic coating.

In some aspects, the pro-fibrotic coatings of the invention include a pro-fibrotic agent, such as a pro-fibrotic polymer, that is immobilized on the surface of an implantable medical device through use of one or more latent reactive groups. The latent reactive groups, such as photoreactive groups, can be pendent from the pro-fibrotic polymer, independent of the pro-fibrotic polymer, or both. Photoreactive groups can be pendent from the pro-fibrotic polymer and activated to bind pro-fibrotic polymer to the surface of the device, or to one or more other components, such as polymeric components present in the coating.

In some preferred aspects, the photoreactive group includes an aryl ketone, for example, acetophenone, benzophenone, anthraquinone, anthrone, and anthrone-like heterocycles (i.e., heterocyclic analogs of anthrone such as those having N, O, or S in the 10-position), or their substituted (e.g., ring substituted) derivatives. Examples of preferred aryl ketones include heterocyclic derivatives of anthrone, including acridone, xanthone and thioxanthone, and their ring substituted derivatives.

In some aspects of the invention the pro-fibrotic coating includes a pro-fibrotic polymer, a photoreactive group, and a polymerizable group. The polymerizable group is preferably pendent from a polymer, such as the pro-fibrotic polymer or, optionally, another polymer that is not the pro-fibrotic polymer. The polymer can have one or more polymerizable groups. For example, in some aspects, the polymerizable group can be an ethylenically unsaturated group that is pendent from the pro-fibrotic polymer. Activation of the polymerizable group can promote free radical polymerization of the pro-fibrotic polymer and the formation of a coating on the surface. Polymerization initiation can be carried out by activation of the photoreactive group.

Polymerization of the pro-fibrotic polymer having a polymerizable group can form a coated layer of pro-fibrotic polymers bonded to one another, or if other polymerizable material is included in the coating, pro-fibrotic polymers bonded to one another and the other material present in the coating. In this aspect, bonding between the surface of the device and the pro-fibrotic polymer is not required.

The pro-fibrotic polymer can be based on a natural polymer, such as collagen, or a synthetic polymer.

In another aspect of the invention the pro-fibrotic coating includes a pro-fibrotic cationic polymer and a photoreactive group. In forming the coating, the photoreactive group can be activated to covalently bind the pro-fibrotic cationic polymer to the surface of the article. The pro-fibrotic cationic polymer can strongly draw platelets and proteins involved in promoting the formation of a fibrin clot to the coated surface.

In another aspect of the invention the pro-fibrotic coating includes non-animal derived pro-fibrotic polymer and photoreactive group. The non-animal derived pro-fibrotic polypeptide can be a peptide having collagen activity, such as synthetic collagen.

In this aspect, improved safety of the coated article can be achieved because these coatings do not rely on the presence of animal-derived materials, such as bovine collagen, which could be potentially associated with animal-derived contaminants. Therefore, in these aspects, the use of the non-animal derived pro-fibrotic materials greatly reduces, if not eliminates, the possibility that animal-derived contaminants will be introduced into the body. Use of the pro-fibrotic coatings of the invention can also improve the overall quality and consistency of the coatings as use of materials from animal preparations having potential batch-to-batch variations is circumvented.

In another aspect of the invention, the pro-fibrotic coatings include a pro-fibrotic agent, such as a pro-fibrotic polymer, and a thromboresistant agent, which are both present in the coating. The thromboresistant agent present in the pro-fibrotic coating can modulate the fibrotic response as initiated by the pro-fibrotic agent as well as improve the properties of the coating.

The thromboresistant agent can modulate the rate of the fibrotic response so that an appropriate clot is formed in the vicinity of the coated article. The presence of the thromboresisant agent is not to prevent clot formation but rather to modulate the rate and extent of clot formation in order to avoid potentially problematic consequences of clot formation, such as embolus.

Therefore, in another aspect of the invention, the pro-fibrotic coating includes a pro-fibrotic agent, a thromboresistant agent, and a photoreactive group. In one aspect of the invention, the pro-fibrotic agent is a pro-fibrotic polymer. Various synthetic or natural pro-fibrotic polymers, such as collagen, can be used.

The photoreactive group can be pendent from or independent of the pro-fibrotic polymer and/or the thromboresistant agent. In some aspects the photoreactive group is present on a crosslinking moiety that can bond the pro-fibrotic polymer to the thromboresistant agent.

In some cases the independent photoreactive groups can serve as a coupling moiety, when activated able to couple the pro-fibrotic agent and/or thromboresistant agent to the surface of the device or to another component to form the pro-fibrotic coating. For example, the pro-fibrotic polymer, such as collagen, can include a pendent photoreactive group that has been reacted to bond pro-fibrotic polymer to the thromboresistant agent.

In other aspects, photoreactive group is present on a polymerization initiator, and the initiator is activated to promote formation of one or more coated layers of polymerized material, wherein the polymerized material is the pro-fibrotic polymer, the thromboresistant agent, or combinations thereof. For example, the coating may include a layer comprising a pro-fibrotic polymer, such as collagen, bonded via reacted polymerizable groups, a layer comprising the thromboresistant agent bonded via reacted polymerizable groups, or a layer comprising a combinations of bonded pro-fibrotic polymer and thromboresistant agent. The coating can also include combinations of these layers.

In one aspect, the coating includes a layer comprising PEG bonded via reacted polymerizable groups, and a layer comprising collagen bonded via reacted polymerizable groups.

The invention also contemplates various methods for forming a pro-fibrotic coating on a medical article. The method includes a step of disposing a first composition comprising a thromboresistant agent, a step of disposing a second composition comprising collagen, and a step of activating the photoreactive groups to form the pro-fibrotic coating. In this method the photoreactive groups can be present in the first coating composition, present in the second coating composition, independent of the first and second coating composition, or combinations thereof.

Another method for forming a pro-fibrotic coating on a medical article includes steps of disposing a composition comprising a collagen and a thromboresitant agent, and activating the photoreactive groups to form the pro-fibrotic coating. In this method photoreactive groups are present in the first coating composition, second coating composition, independent of the first and second coating composition, or combinations thereof.

Yet another method for forming a pro-fibrotic coating on a medical article includes the step of disposing a first composition comprising a thromboresitant polymer comprising polymerizable groups, disposing a second composition comprising collagen comprising polymerizable groups, and activating the polymerization initiator to form the pro-fibrotic coating. In these methods the polymerization initiator is present in the first coating composition, second coating composition, independent of the first and second coating composition, or combinations thereof.

Optional materials can be added to the pro-fibrotic coating. One class of preferred polymerizable materials include hydrophilic or swellable polymers having pendent polymerizable groups. These types of polymers can be useful in pro-fibrotic coatings as they can provide space-filling properties to the coated device. Such materials are able to improve article performance by contributing to the overall function of the device, for example, by improving sealant function or by improving the ability of the article to occlude an area of the body.

Therefore, in another aspect of the invention, coating can be formed from a coating composition that includes a swellable polymer, a pro-fibrotic polymer, and a photoreactive group. In some cases the swellable polymer may also provide throboresistant properties, such as PEG.

DETAILED DESCRIPTION

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

The compounds, composition, methods, and devices of the invention can be used for promoting a pro-fibrotic response from an article coated with the pro-fibrotic materials of the invention. The pro-fibrotic response can promote formation of a fibrin clot in association with the article which can provide a space-filling function useful for establishing hemostatsis or occlusion in the vicinity of the article.

According to the invention, a pro-fibrotic coating is provided on a surface of a medical article. The medical article can be any article that is introduced into a mammal for the prophylaxis or treatment of a medical condition, wherein it is desired to promote formation of a fibrin clot in association with the coated article. These articles can be introduced subcutaneously, percutaneously, or surgically to rest within an organ, tissue, or lumen of an organ, such as arteries, veins, ventricles or atria of the heart. The medical article having the pro-fibrotic coating can provide one or more functions, including providing a barrier to the movement of body fluids, such as blood.

A medical article having a pro-fibrotic coating can also be prepared by assembling an article having two or more "parts" (for example, pieces of a medical article that can be put together to form the article) wherein at least one of the parts has a pro-fibrotic coating. All or a portion of the part of the medical article can have a pro-fibrotic coating. In this regard, the invention also contemplates parts of medical articles (for example, not the fully assembled article) that have a pro-fibrotic coating.

The pro-fibrotic coatings can be formed on the surface of articles that are intended to have a hemostatic function, providing a barrier to the movement of body fluids. In many cases it is desirable to form these artificial barriers to ensure that the implanted article functions as it is intended to in the body. For example, in some cases the pro-fibrotic coatings promote the formation of a barrier that prevents fluids from moving from one place to another within the body, while in other cases it provides a barrier that prevents fluids from moving into an area within the body, such as an aneurysm.

After the pro-fibrotic coating promotes formation of a fibrin clot that is associated with the surface of the device, the clotted area generally becomes impermeable to the movement of body fluids. Impermeable, as used in relation to the function of the fibrin-clotted area, refers to a significant reduction in the transmission of bulk liquid or fluids through or into the clotted area. For example, the clotted area can be impermeable to the transmission of blood.

The pro-fibrotic polymer can be used to provide a coating to a wide variety of articles. As used herein, "article" is used in its broadest sense and includes objects such as medical devices. Such articles include, but are not limited to vascular implants and grafts, grafts, surgical devices; synthetic prostheses; vascular prosthesis including endoprosthesis, stent-graft, and endovascular-stent combinations; small diameter grafts, abdominal aortic aneurysm grafts; wound dressings and wound management device; hemostatic barriers; mesh and hernia plugs; patches, including uterine bleeding patches, atrial septal defect (ASD) patches, patent foramen ovale (PFO) patches, ventricular septal defect (VSD) patches, and other generic cardiac patches; ASD, PFO, and VSD closures; percutaneous closure devices, mitral valve repair devices; left atrial appendage filters; valve annuloplasty devices, catheters; central venous access catheters, vascular access catheters, abscess drainage catheters, drug infusion catheters, parental feeding catheters, intravenous catheters (e.g., treated with antithrombotic agents), stroke therapy catheters, blood pressure and stent graft catheters; anastomosis devices and anastomotic closures; aneurysm exclusion devices; biosensors including glucose sensors; birth control devices; breast implants; cardiac sensors; infection control devices; membranes; tissue scaffolds; tissue-related materials; shunts including cerebral spinal fluid (CSF) shunts, glaucoma drain shunts; dental devices and dental implants; ear devices such as ear drainage tubes, tympanostomy vent tubes; ophthalmic devices; cuffs and cuff portions of devices including drainage tube cuffs, implanted drug infusion tube cuffs, catheter cuff, sewing cuff; spinal and neurological devices; nerve regeneration conduits; neurological catheters; neuropatches; orthopedic devices such as orthopedic joint implants, bone repair/augmentation devices, cartilage repair devices; urological devices and urethral devices such as urological implants, bladder devices, renal devices and hemodialysis devices, colostomy bag attachment devices; biliary drainage products.

In some embodiments the pro-fibrotic coatings are used in conjunction with an occlusion device for occluding any sort of target area within the body. Occlusion devices include implantable medical devices that are delivered to a target area of the body and that are intended to function to prevent movement of body fluids through or into the area in which the device has been delivered (for example, a hemostatic function). Thrombosis and the formation of a clot in association with the occlusion device generally aid in establishing the hemostatic function. Occlusion can be established by delivering the device to a target area and allowing the pro-fibrotic coating to promote formation of fibrin clot, thereby physically occluding the target area. While the occlusion articles having the pro-fibrotic coatings are particularly useful for the selective occlusive of vasculature, including both arteries, veins, fistulas and aneurysms, these coated devices can also be used in other body lumens, such as the fallopian tubes, bile ducts, and the like. The pro-fibrotic coatings are particularly useful in connection with vascular occlusion coils, wires, or strings that can be inserted into aneurysms.

In an exemplary method, a vascular occlusion coil having a pro-fibrotic coating is delivered into an aneurysm. The pro-fibrotic coating is able to promote a fibrotic response, causing the rapid accumulation of clotting components within the aneurysm. Gradually, and preferably, the clot occludes the aneurysm preventing the inflow of blood thereby substantially reducing the risk that the aneurysm will rupture. In some aspects, the invention is directed at preparing and utilizing a vascular occlusion coil having pro-fibrotic coating that promotes formation of an organized fibrin clot in the aneurysm that is unlikely to dislodge from the aneurysm.

Vascular occulsion devices can include wires, coils, braids, and strings, and can have a helically wound configuration. Exemplary coils are generally 2.2 mm or less in diameter, more particularly in the range of 0.2 mm to 2.2 mm and can be composed of wires 1.25 mm or less in diameter, for example in the range of 0.125 mm to 1.25 mm. An exemplary length of the device is typically in the range of 0.5 to 100 centimeters In some embodiments, the vascular occlusion device is prepared from metal such as platinum, gold, or tungsten, although other metals such as rhenium, palladium, rhodium, ruthenium, titanium, nickel, and alloys of these metals, such as stainless steel, titanium/nickel, and nitinol alloys, can be used. A preferred metal coil includes primarily platinum.

In another embodiment, the vascular occlusion device includes a polymeric string, wire, or coil. Particularly useful devices include polymers having hydrogel properties. Useful polymers for this type of device include poly(urethanes), poly(acrylates), poly(methacrylates), poly(vinylpyrrolidone), cellulose acetate, ethylene vinyl alcohol copolymers, poly(acrylonitrile), poly(vinylacetate), cellulose acetate butyrate, nitrocellulose, copolymers of urethane/carbonate, copolymers of styrene/maleic acid, or mixtures thereof.

In some embodiments, the polymeric string includes a stiff hydrogel core and a surrounded by soft hydrogel foam which is surrounded by a gel outer coating. In other embodiments of the coil or string includes soft biocompatible polymers such as ePTFE, urethanes, polyolefins, and nylons.

The pro-fibrotic materials of the invention can be disposed on the hydrogel surface of these devices and then irradiated to activate the photoreactive groups and to form a coating that includes the pro-fibrotic polymer.

The invention also provides methods of preparing pro-fibrotic coatings on porous surfaces of medical articles. The pro-fibrotic polymers of the invention can be disposed on a porous surface of a medical article to form a pro-fibrotic coating. The porous surface can be constructed from one or a combination of similar or different biomaterials. A pro-fibrotic coating composition can be prepared and/or applied in such a manner as to fill the pores on the surface of the article with the coating material. This can be achieved by, for example, controlling factors such as the viscosity of the coating composition and the activation of the photoreactive groups that are used to associate the pro-fibrotic polymers with the surface of the device.

An article having a "porous surface" refers to any article having a surface with pores on which a pro-fibrotic coating can be formed. The pores are preferably of a physical dimension that permits in-growth of tissue into the pores. The porous surface can be associated with a non-porous surface, such as a scaffold that can provide support to the porous surface.

The medical article can include porous surfaces that can be provided with a pro-fibrotic coating and non-porous surfaces that are not coated with the pro-fibrotic coating, optionally coated with the pro-fibrotic coating, or coated with a material that is different than the pro-fibrotic coating. All or a portion of the porous surfaces can be coated with the pro-fibrotic coating.

In many cases the porous surface of the article is a fabric or has fabric-like qualities. The porous surface can be formed from textiles, which include woven materials, knitted materials, and braided materials. Particularly useful textile materials are woven materials which can be formed using any suitable weave pattern known in the art.

The porous surface can be that of a graft, sheath, cover, patch, sleeve, wrap, casing, and the like. These types of articles can function as the medical article itself or be used in conjunction with another part of a medical article (examples of which are described in further detail herein).

For example, the pro-fibrotic coatings can be used in conjunction with fabrics, such as cardiac patches, sheaths, and grafts. In these embodiments, the pro-fibrotic coatings can be used to generate a hemostatic fibrin clot in association with the coated fabric. These coated articles can be used to prevent the flow of blood within the body in the location the coated article is intended to function.

The porous surface can include any suitable type of biomaterial. Useful biomaterials can be woven into fibers for the preparation of fabrics as described herein. Useful materials include synthetic addition or condensation polymers such as polyesters, polypropylenes, polyethylenes, polyurethanes, and polytetrafluoroethylenes. Polyethylene terephthalate (PET) is a commonly used polymer in fabrics. Blends of these polymers can also be utilized in the preparation of fibers, such as monofilament or multi-filament fibers, for the construction of fabrics. Commonly used fabrics include those such as nylon, velour, and DACRON™.

The fabrics can optionally include stiffening materials to improve the physical properties of the article, for example, to improve the strength of a graft. Such materials can improve the function of an implanted article. For example, strengthening materials can improve the patency of the graft.

Porous surfaces can also be formed by dipping mandrels in these types of polymers.

Surgical patches can be used in various medical procedures to prevent blood flow. A surgical patch having the inventive pro-fibrotic coating as described herein is directed at rapidly generating a fibrin clot associated with the patch, thereby improving hemostatic function.

Other particular contemplated porous surfaces include those of cardiac patches. These can be used to decrease suture line bleeding associated with cardiovascular reconstructions. The patches can be used to seal around the penetrating suture. Common materials used in cardiac patches include PTFE and DACRON™.

The thickness of the material used as the porous surface can be chosen depending on the application. However, it is common that these thicknesses are about 1.0 mm or less on average, and typically in the range of about 0.10 mm to about 1.0 mm.

Other particular contemplated porous surfaces include grafts, particularly grafts having textured exterior portions. Examples of textured grafts include those that have velour-textured exteriors, with textured or smooth interiors. Grafts constructed from woven textile products are well known in the art and have been described in numerous documents, for example, U.S. Pat. Nos. 4,047,252; 5,178,630; 5,282,848; and 5,800,514, the disclosures of which are incorporated in their entirety herein by reference.

The medical articles can be fabricated from any suitable biomaterial or combinations of biomaterials. Preferred biomaterials include those formed of synthetic polymers, including oligomers, homopolymers, and copolymers resulting from either addition or condensation polymerizations. Examples of suitable addition polymers include, but are not limited to, acrylics such as those polymerized from methyl acrylate, methyl methacrylate, hydroxyethyl methacrylate, hydroxyethyl acrylate, acrylic acid, methacrylic acid, glyceryl acrylate, glyceryl methacrylate, methacrylamide, and acrylamide; vinyls such as ethylene, propylene, vinyl chloride, vinyl acetate, vinyl pyrrolidone, and vinylidene difluoride. Examples of condensation polymers include, but are not limited to, nylons such as polycaprolactam, polylauryl lactam, polyhexamethylene adipamide, and polyhexamethylene dodecanediamide, and also polyurethanes, polycarbonates, polyamides, polysulfones, poly(ethylene terephthalate), polylactic acid, polyglycolic acid, polydimethylsiloxanes, and polyetherketone.

A pro-fibrotic "coating" as used herein can include one or more "coated layers", each coated layer including one or more coating materials.

In some cases, the pro-fibrotic coating consists of a single layer of material that includes the pro-fibrotic polymer. In other cases, the coating includes more than one coated layer, at least one of the coated layers including the pro-fibrotic polymer. If more than one layer is present in the pro-fibrotic coating, the layers can be composed of the same or different materials. While the coated layers can include the same or different coating materials, a coated layer that includes the pro-fibrotic polymer is generally made available to body fluids upon or after implanting the coated article in the body.

Having multiple coated layers can be particularly useful when it is desired to form a coating that provides a space-filling function in association with the article. The coated material on the article surface physically occupies space in an area of the body that receives the article having the pro-fibrotic coating.

The pro-fibrotic coating materials can be disposed on any surface suitable for the immobilization of the pro-fibrotic coating materials. In many aspects the pro-fibrotic materials are disposed on a surface which can be reacted with the photoreactive group. In other words, the photoreactive group can form a covalent bond with the surface material, thereby associating the pro-fibrotic coating materials with the surface.

All or a portion of the surface of the device can have an intermediate or base coated layer that facilitates the immobilization of the pro-fibrotic materials. This may also be called a "tie layer" or a "binding layer". The tie layer can provide a material to which the photoreactive groups can react with and form a covalent bond. Suitable base or intermediate coatings include an abstractable hydrogen material. These can also include functionalities such as reactive groups or silane groups. Polymers are preferred materials for use with the intermediate layer.

In some aspects of the invention the medical article is a metal or metal alloy-containing vascular occlusion coil or wire that includes a pro-fibrotic coated layer and an intermediate layer located between the metal-containing wire or coil and the pro-fibrotic layer. The intermediate layer can be useful for associating the pro-fibrotic layer with the coil. For example, the intermediate layer can serve as a target for the photoreactive groups, allowing the pro-fibrotic polymer to be coupled to the wire or coil. The intermediate layer can include a polymer or other suitable compound that is reactive with the activated photoreactive groups of the invention. The polymer or other suitable compound can be silane-containing, or can have reactive functionalities such as amino groups.

In other aspects of the invention, the vascular occlusion article is a cylindrically-shaped article of polymeric material, such as a polymeric string, on which the pro-fibrotic coating can be disposed. The vascular occlusion article can include polymer material that has hydrogel properties. The photoreactive group associated with the coating materials can be activated to form the pro-fibrotic coating. For example, a pro-fibrotic polymer having a pendent photoreactive group can be covalently bonded to the hydrogel surface via the photoreactive group.

Generally, the coating process can be performed to coat all of or desired portions of the medical article. The coating process can be directed based on the intended function of the article. In some cases, it may be desirable to generate a pro-fibrotic response on only a portion of the article. For example, in the case of vascular occlusion coils, wires, or strings, it may be desirable only to coat the portion of the coil, wire, or string that is inserted into an aneurysm.

The materials used for forming a pro-fibrotic coating can be disposed on the surface using any suitable coating method. Such methods include, but are not limited to, spray coating, dipping, injecting, and brushing. A preferred method for coating the surface of a medical article using the compounds described herein is by spray coating.

In some aspects of the invention, the pro-fibrotic polymer is a natural polymer, such as a peptide or protein. Examples of pro-fibrotic peptides or proteins include, but are not limited to, for example, thrombin and collagen, such as, recombinant human collagen (FibroGen, South San Francisco, Calif.). Collagen peptides and modified collagen can be used in the preparation of the pro-fibrotic coating. Other contemplated pro-fibrotic polypeptides are described herein.

In one embodiment the pro-fibrotic coatings include a non-animal derived pro-fibrotic polypeptide. As used herein, an "animal" refers to a non-human animal that typically is used as livestock and includes animals such as cows (bovine), pig (porcine), and chicken, from which collagen is typically extracted.

Other useful pro-fibrotic agents can include platelet factors 1-4, platelet activating factor (acetyl glyceryl ether phosphoryl choline); P-selectin and von Willebrand factor (vWF); tissue factor; plasminogen activator initiator-1; thromboxane; procoagulant thrombin-like enzymes including cerastotin and afaâcytin; phospholipase $A_2$; $Ca^{2+}$-dependent lectins (C-type lectin); factors that bind glycoprotein receptors and induce aggregation including aggretin, rhodocytin, aggregoserpentin, triwaglerin, and equinatoxin; glycoprotein Ib agonists including mamushigin and alboaggregin; vWF interacting factors including botrocetin, bitiscetin, cerastotin, and ecarin.

Other factors, including protein factors, that are involved in the clotting cascade include coagulation factors I-XIII (for example, fibrinogen, prothrombin, tissue thromboplastin, calcium, proaccelerin (accelerator globulin), proconvertin (serum prothrombin conversion accelerator), antihemophilic factor, plasma thromboplastin component, Stuart factor (autoprothrombin C), plasma thromboplastin antecedent (PTA), Hageman factor, and fibrin-stabilizing factor (FSF, fibrinase, protransglutaminase)).

In some aspects, the pro-fibrotic coatings include a pro-fibrotic cationic polymer.

The pro-fibrotic cationic polymer is preferably a polymer conveying a positive charge sufficient to attract platelets and clotting factors to the surface of the coated device. The pro-fibrotic cationic polymer can include, for example, primary amine groups. Exemplary cationic polymers include dextrans and polyimines having amine groups, for example, DEAE dextran (diethyleneaminoethyl dextran) and polyethyleneimine (PEI). A preferred synthetic pro-fibrotic cationic polymer is polyethyleneimine. Exemplary naturally-occurring cationic polymers include chitin and chitosan (D-acetylated chitin).

The pro-fibrotic cationic polymer can be a homopolymer or a copolymer. The pro-fibrotic coating can also include blends of different cationic polymers that can promote a pro-fibrotic response.

Other suitable pro-fibrotic cationic polymers include positively charged groups such as ternary or quaternary cationic groups. Examples of suitable ternary or quaternary cationic groups include quaternary ammonium, quaternary phosphonium, and ternary sulfonium groups. These polymers can be prepared by various techniques. Polymers having primary, secondary, tertiary amines, or combinations thereof, can be quaternized, resulting in the formation of charged quaternary amine groups on the polymer. Amines can be successively alkylated, by, for example, alkyl halides, to provide a quaternary amine via the Menshutkin reaction.

Various schemes can be used to prepare a pro-fibrotic cationic polymer having pendent photoreactive groups. For example, a pro-fibrotic cationic polymer having pendent photoreactive groups can by synthesized by reacting a polymer having a tertiary amine with a photoreactive group derivatized with a benzyl halide. This reaction allows for the coupling of the photoreactive group to the polymer and at the same time converting the tertiary amine group to a charged quaternary amine group.

A pro-fibrotic cationic polymer having pendent photoreactive groups can also be by synthesized by copolymerizing monomers having photoreactive groups with monomers having cationic groups. In some embodiments an individual monomer having both a photoreactive group and a cationic group can be used to prepare the pro-fibrotic cationic polymer. Optionally, other monomers can be included in a copolymerization reaction. Methods of preparing the pro-fibrotic cationic polymer are exemplified herein.

Alternatively, or additionally, the photoreactive group can be activated to covalently bind the pro-fibrotic cationic polymer to another pro-fibrotic cationic polymer, or another component, if present, in the coating composition. Generally this approach can be used to promote the formation of a coated layer including the pro-fibrotic cationic polymer on the surface of an article.

It is generally desired to use a pro-fibrotic polymer having a size suitable for forming a coating and generating a fibrotic response. In some aspects of the invention the coating includes a pro-fibrotic cationic polymer having a weight average molecular weight ($M_w$) of at least about $2 \times 10^3$ Da, and preferably in the range of about $2 \times 10^3$ Da to $2 \times 10^6$ Da.

In some aspects of the invention the pro-fibrotic polymer has one or more pendent photoreactive groups. Pendent photoreactive groups can be located along the length of the pro-fibrotic polymer, at one or both termini of the polymer, or both. The arrangement of photoreactive group on the pro-fibrotic polymer can provide for the formation of the pro-fibrotic coating on the surface of the article.

A photoreactive group includes one or more reactive moieties that respond to a specific applied external energy source, such as radiation, to undergo active species generation, for example, active species such as nitrenes, carbenes and excited ketone states, with resultant covalent bonding to an adjacent targeted chemical structure. Examples of such photoreactive groups are described in U.S. Pat. No. 5,002,582. Photoreactive groups can be chosen to be responsive to various portions of the electromagnetic spectrum, typically ultraviolet, visible or infrared portions of the spectrum. "Irradiation" refers to the application of electromagnetic radiation to a surface.

Photoreactive aryl ketones are one type of preferred photoreactive groups that can be pendent from the pro-fibrotic polymer. Examples of photoreactive aryl ketones include, but are not limited to, acetophenone, benzophenone, anthraquinone, anthrone, and anthrone-like heterocycles (i.e., heterocyclic analogs of anthrone such as those having N, O, or S in the 10-position), or their substituted (e.g., ring substituted) derivatives. Examples of preferred aryl ketones include heterocyclic derivatives of anthrone, including acridone, xanthone and thioxanthone, and ring substituted derivatives.

Other suitable photoreactive groups include azides, for example, arylazides ($C_6R_5N_3$) such as phenyl azide and particularly 4-fluoro-3-nitrophenyl azide, acyl azides (—CO—$N_3$) such as ethyl azidoformate, phenyl azidoformate, sulfonyl azides (—$SO_2$—$N_3$) such as benzensulfonyl azide, and phosphoryl azides $(RO)_2PON_3$ such as diphenyl phosphoryl azide and diethyl phosphoryl azide.

Yet other suitable photoreactive groups include diazo compounds, for example, diazoalkanes (—$CHN_2$) such as diazomethane and diphenyldiazomethane, diazoketones (—CO—$CHN_2$) such as diazoacetophenone and 1-trifluoromethyl-1-diazo-2-pentanone, diazoacetates (—O—CO—$CHN_2$) such as t-butyl diazoacetate and phenyl diazoacetate, and beta-keto-alpha-diazoacetates (—CO—$CN_2$—CO—O—) such as 3-trifluoromethyl-3-phenyldiazirine, and ketenes (—CH=C=O) such as ketene and diphenylketene.

Exemplary photoreactive groups are shown as follows in Table 1.

TABLE 1

| Photoreactive Group | Bond Formed |
| --- | --- |
| aryl azides | Amine |
| acyl azides | Amide |
| Azidoformates | Carbamate |
| sulfonyl azides | Sulfonamide |
| phosphoryl azides | Phosphoramide |
| Diazoalkanes | new C—C bond |
| Diazoketones | new C—C bond and ketone |
| Diazoacetates | new C—C bond and ester |
| beta-keto-alpha-diazoacetates | new C—C bond and beta-ketoester |
| aliphatic azo | new C—C bond |
| Diazirines | new C—C bond |
| Ketenes | new C—C bond |
| photoactivated ketones | new C—C bond and alcohol |

In some embodiments the photoreactive group is independent of the pro-fibrotic polymer. For example, an independent photoreactive group can be a part of a photoreactive crosslinking compound. When activated, the photoreactive group of the photoreactive crosslinking compound can couple the pro-fibrotic polymer to the surface of the device, to another component in the coating composition, or to another coated layer to form the pro-fibrotic coating. Suitable photoreactive crosslinking agents can have two or more photoreactive groups. The photoreactive crosslinking agents can have the same or different photoreactive groups. Exemplary photoreactive crosslinking agents are described in Applicant's U.S. Pat. No. 5,414,075 (Swan et al.), and U.S. Publication No. 2003/0165613 A1 (Chappa et al.). See also U.S. Pat. No. 5,714,360 (Swan et al.) and U.S. Pat. No. 5,637,460 (Swan et al.).

In another aspect, a compound comprising a photoreactive group is used as a photoinitiator, for example, to promote the polymerization of agents having polymerizable groups, such as a pro-fibrotic polymer having polymerizable groups.

In another embodiment of the invention the pro-fibrotic coating includes a pro-fibrotic polymer, a photoreactive group, and a polymerizable group. In some cases the polymerizable group is pendent from the pro-fibrotic polymer. For example, the pro-fibrotic polymer, such as collagen, can be modified to have one or more polymerizable groups. In other cases, the polymerizable group is present on a compound that is not the pro-fibrotic polymer. In some preferred embodiments the polymerizable group is pendent from another polymer, such as a polymeric thromboresistant agent or a hydrophilic polymer as described herein.

The polymerizable group can be an ethylenically unsaturated group selected from vinyl groups, acrylate groups, methacrylate groups, ethacrylate groups, 2-phenyl acrylate groups, acrylamide groups, methacrylamide groups, itaconate groups, and styrene groups.

In the case where a polymerizable material is present in a pro-fibrotic coating composition, the photoreactive group can promote initiation of a free radical polymerization reaction leading to the formation of a coated layer of polymerized material. Other agents that facilitate formation of a polymerized layer can be present in the composition. These can include, for example, polymerization accelerants which can improve the efficiency of polymerization. Examples of useful accelerants include N-vinyl compounds, particularly N-vinyl pyrrolidone and N-vinyl caprolactam. Such accelerants can be used, for instance, at a concentration of between about 0.01% and about 5%, and preferably between about 0.05% and about 0.5%, by weight, based on the volume of the coating composition.

In another aspect of the invention, the pro-fibrotic coatings include a pro-fibrotic agent, such as a pro-fibrotic polymer, and a thromboresistant agent, which are both present in the coating.

Different approaches can be implemented to modulate the rate and extent of clot formation using the combination of pro-fibrotic and thromboresistant agents in association with the coating on the article. For example, the pro-fibrotic polymer and the thromboresistant agent can be dispersed or blended together in a single layer of the coating, or can be associated with the coating independently of one another, such as in separate layers. The manner in which the pro-fibrotic polymer and thromboresistant agent are associated with the coated article may depend on the particular polymer and agent chosen, as well as the medical article surface characteristics (for example, material, porosity, and configuration).

In some cases, the pro-fibrotic polymer and thromboresistant agent can be combined in a coating composition and deposited on the medical article. In the coating composition, for example, precise quantities of pro-fibrotic agent and thromboresistant agent can be present in order to form a coating designed to achieve an appropriate rate and extent of clot formation. In other cases, the ratio of pro-fibrotic agent to thromboresistant agent can be set in order to form a coating designed to achieve an appropriate rate and extent of clot formation. One of skill in the art, given the present teaching, can select any one or more of the pro-fibrotic agents and any one or more thromboresistant agents to provide the desired effect.

In one aspect of the invention, it has been found that coating compositions including an amount of throboresistant agent of about 10% or greater provide exceptional pro-fibrotic coatings. For example, the thromboresistant agent can be one with polymerizable groups, such as a PEG macromer.

In yet other cases, the pro-fibrotic agent can be associated with the coating in a manner that allows blood components to come into contact with the pro-fibrotic agent before blood components come into contact with the thromboresistant agent. For example, a coating can be prepared having a layer that includes the pro-fibrotic agent, and a layer that includes the thromboresistant agent, wherein the layer that includes the thromboresistant agent is proximal to the surface of the coated article. An exemplary coating includes a first coated layer with PEG proximal to the surface and a second coated layer with collagen.

In some embodiments, the pro-fibrotic coating includes a pro-fibrotic agent, a thromboresistant agent, a photoreactive group, and a polymerizable group. In some cases the polymerizable group is pendent from a pro-fibrotic polymer. For example, the pro-fibrotic polymer can be modified to have one or more polymerizable groups. In other cases the polymerizable group is pendent from a thromboresistant polymer. In yet other cases, the polymerizable group is present on a compound that is not the pro-fibrotic polymer. In some preferred embodiments the polymerizable group is pending form another polymer, such as a hydrophilic polymer as described herein. It is also envisioned that a coating composition can include two or more different compounds, such as polymers, having polymerizable groups.

In some aspects the coating includes a pro-fibrotic agent and a thromboresistant agent, wherein the thromboresistant agent includes pendent photoreactive groups. The coating can be formed by disposing a composition that includes a pro-fibrotic agent and a thromboresistant agent on a surface and then treating the surface to activate the photoreactive group pendent from the thromboresistant agent to form the coating. For example, the thromboresistant agent having pendent photoreactive group(s) can be selected from photoderivitized heparin and photoderivitized hyaluronic acid, photoderivitized lysine-derivatized vinyl polymers, photo-derivitaized PEG, and photoderivitized fatty acid.

The thromboresistant agent can modulate the rate of the fibrotic response so that an appropriate clot is formed in the vicinity of the coated article.

One preferred thromboresistant agent is polyethylene glycol (PEG). Surfaces covered with polyethylene glycol have been shown to be biocompatible because PEG's properties yield nonimmunogenicity, nonantigenicity, and protein rejection.

PEG can be immobilized in the coating using photoreactive groups. In some aspects the coating is formed using PEG having polymerizable groups. A coated layer comprising PEG can be formed by disposing a coating composition including acrylated PEG in combination with a polymerization initiator, such a polymerization initiator having photoreactive groups.

Other examples of thromboresistant agents include heparin, heparin derivatives, sodium heparin, low molecular weight heparin, hirudin, lysine, prostaglandins, argatroban, forskolin, vapiprost, prostacyclin and prostacyclin analogs, D-ph-pr-arg-chloromethylketone (synthetic antithrombin), dipyridamole, glycoprotein IIb/IIIa platelet membrane receptor antibody, coprotein IIb/IIIa platelet membrane receptor antibody, recombinant hirudin, thrombin inhibitor (such as commercially available from Biogen), chondroitin sulfate, modified dextran, albumin, streptokinase, tissue plasminogen activator (TPA), urokinase, nitric oxide inhibitors, and the like. The thromboresistant agent can also be an inhibitor of the GPIIb-IIIa platelet receptor complex, which mediates platelet aggregation. GPIIb/IIIa inhibitors can include monoclonal antibody Fab fragment c7E3, also know as abciximab (ReoPro™), and synthetic peptides or peptidomimetics such as eptifibatide (Integrilin™) or tirofiban (Agrastat™).

Optionally, a polymer or compound that is different than the pro-fibrotic agent or the thromboresistant agent can be included in the pro-fibrotic coating. The polymer or compound can be selected to change or improve the properties of the pro-fibrotic coating that is formed by the pro-fibrotic and thromboresistant agents. For example, the polymer or compound can change the elasticity, flexibility, wettability, or adherent properties, (or combinations thereof) of the coating formed on the surface.

Application techniques for the coating of the pro-fibrotic and thromboresistant materials include, for example, dipping, spraying, brushing, and the like. The suitability of the polymeric composition for use with a particular medical article, and in turn, the suitability of the application technique, can be evaluated by those skilled in the art, given the present description.

The pro-fibrotic polymer can be dispersed or blended together with another agent useful for forming the pro-fibrotic coating. These can include other non-fibrotic or non-thromboresistant polymeric materials.

Optionally, a polymer or compound that is different than the pro-fibrotic agent can be included in the pro-fibrotic coating. The polymer or compound can be selected to change or improve the properties of the pro-fibrotic coating that is formed by the pro-fibrotic polymer. For example, the polymer or compound can change the elasticity, flexibility, wettability, or adherent properties, (or combinations thereof) of the coating formed on the surface.

In some aspects, hydrophilic or swellable polymers can be included in the coating containing the pro-fibrotic polymer. These types of polymers can be useful in pro-fibrotic coatings as they can provide space-filling properties to the coated device. Such materials are also able to improve article performance by contributing to the overall function of the device, for example, by improving sealant function or by improving the ability of the article to occlude an area of the body.

The hydrophilic or swellable polymer can include pendent polymerizable groups and can be used in a method to form a coated layer that can include the pro-fibrotic polymer, or can be separate from the pro-fibrotic polymer.

For example, a composition including a hydrophilic or swellable polymer having pendent polymerizable groups and a polymerization initiator can be disposed on a surface of a device. A coated layer containing the hydrophilic or swellable polymer can be formed by initiating polymerization of the polymers. Subsequently, a composition including the pro-fibrotic polymer can be disposed on the surface. The pro-fibrotic polymer can also include polymerizable groups. A coated layer containing the pro-fibrotic polymer can be formed on the layer that includes the hydrophilic or swellable polymer by initiating polymerization of the polymers pro-fibrotic polymer.

Particularly useful hydrophilic or swellable polymers include poly(vinylpyrrolidone) (PVP), poly(ethylene glycol) (PEG), poly(ethylene oxide), poly(ethyloxazoline), poly(propylene oxide), polyacrylamide (PAA), poly(vinyl alcohol) (PVA), copolymers thereof, and the like. One or more polymerizable groups can be pendent from the swellable polymer. Mixtures of swellable polymers can also be used.

In some aspects, the hydrophilic or swellable polymer may have thromboresistant properties, such as PEG.

While it can be useful to incorporate swellable polymers having pendent polymerizable groups into the pro-fibrotic coatings, swellable polymers without pendent polymerizable groups can also be utilized to form the coating. Therefore, in another aspect of the invention, coating can be formed from a coating composition that includes a swellable polymer, a pro-fibrotic polymer, and a photoreactive group.

Application techniques for the coating of the pro-fibrotic polymer includes, for example, dipping, spraying, brushing, and the like.

A coating with a desired thickness can be formed by disposing the coating materials on a surface, treating the disposed materials to activate the photoreactive groups to form a coated layer, and then repeating the step of disposing and treating to form a coating with multiple coated layers. Drying steps can also be included in the process.

In some aspects of the invention it is desirable to provide a coating that provides a space-filling function as well as a surface that generates a fibrotic response. For example, in the case where it is desired to occlude an area of the body with the article, a pro-fibrotic coating can be formed on the article that can increase the dimensions of the article as well as providing a surface which attracts clot-forming components. In some embodiments, the pro-fibrotic coating has a thickness of greater than 5 microns, and in other embodiments 10 microns or greater.

In some embodiments, the pro-fibrotic coatings of the invention can include one or more bioactive agent(s) that can enhance the function of the pro-fibrotic surface. Contemplated bioactive agents that can be used in combination with the pro-fibrotic polymer include, for example, cell response modifiers, microtubule inhibitors, remodeling inhibitors, statins, steroids, and vasodilators. If the pro-fibrotic coating is bioresorbable, the bioactive agent can be released as the pro-fibrotic material coating degrades.

The invention will be further described with reference to the following non-limiting Examples. It will be apparent to those skilled in the art that many changes can be made in the embodiments described without departing from the scope of the present invention. Thus the scope of the present invention should not be limited to the embodiments described in this application, but only by embodiments described by the language of the claims and the equivalents of those embodiments. Unless otherwise indicated, all percentages are by weight.

EXAMPLE 1

Preparation of PEI-BBA

A photoderivitized polymer having pendent amine groups was prepared.

Polyethylenimine (PEI; 24.2 wt. % solids; 2000 kg/mol Mw; BASF Corp.) was dried under vacuum and 1.09 g of PEI was dissolved in 19 ml of 90:10 (v/v) chloroform:methanol solution. The PEI solution was then chilled to 0° C. in an ice bath. In 2.8 mL chloroform was added 62 mg of BBA-Cl (4-benzoylbenzoyl chloride), which was allowed to dissolve. The BBA-CL chloroform solution was then added to the chilled PEI chloroform:methanol solution with stirring. The reaction was stirred overnight with gradual warming to room temperature. (Thin layer chromatography (TLC) analysis revealed no unreacted BBA-Cl in the mixture after 2.5 hours.) The reaction solution was then transferred into a large flask and one equivalent of concentrated hydrocholoric acid was added along with 77.5 mL deionized water. The organic solvents were removed under vacuum at 40° C. until the aqueous PEI solution was clear in appearance. The aqueous PEI solution was then diluted to a final concentration of 10 mg/mL for use as a coating solution.

EXAMPLE 2

Preparation of Photo-Spaced-PEI

BBA-EAC-NOS (436.5 g/mole; 110 mg; 0.253 mmole; prepared according to Example 2 of U.S. Pat. No. 6,121,027; incorporated herein by reference) in 3.0 ml DMSO (dimethyl sulfoxide) was added to a chilled solution of PEI (2,000,000 g/mole; 1.0 g; $5 \times 10^{-4}$ mole) in 19 ml of $CHCl_3/CH_3OH$ (90/10) with stirring. The solution was warmed to room temperature overnight with stirring. The solution containing the BBA-EAC-NOS-PEI reaction product was then placed in a mixture of 75 ml $H_2O$ and HCl (12 M; 1.9 ml: 23 mmole). The mixture was then placed on a rotary evaporator to remove the organic solvents. Finally the solution was diluted with water to give 10 mg/ml of the BBA-EAC-PEI.

EXAMPLE 3

Synthesis of APTAC-Polyethylenimine (APTAC-PEI) Polymer

Quaternary ammonium groups, in the form of (acrylamidopropyl)trimethylammonium chloride molecules were coupled to a polyethylenimine polymer using the following procedure: Five grams of polyethylenimine (10,000 $M_w$; Polysciences, Warrington, Pa.) were dissolved in 10 ml of deionized water to make a 50% PEI solution. To the 50% PEI solution was added 16 g of a 75% (3-acrylamidopropyl)-trimethylammonium chloride solution (APTAC; Simga-Aldrich Corp., St. Louis, Mo.). The mixture of PEI and APTAC was shaken overnight at 55° C. The resulting product was a viscous, amber-colored solution, which was stored in a sealed vial at room temperature.

Monitoring the vinyl protons of the APTAC molecule by NMR (Nuclear Magnetic Resonance) on a small scale reaction of equivalent concentrations used in the preparation of APTAC-PEI indicated the reaction was 99% complete at room temperature in 16 hours.

Using a 2.4:1 w/w ratio of APTAC to PEI (12 g APTAC to 5 g PEI (10,000 Da)) as described above, it was estimated that the final $M_w$ of APTAC-PEI was approximately 3.4 times greater (34,000 Da) than the $M_w$ of the starting PEI polymer (10,000 Da).

EXAMPLE 4

Synthesis of APTAC-EITC-Polyethylenimine (BBA-EITC-PEI) Polymer

The APTAC-PEI polymer as synthesized in Example 3 is dried under vacuum and dissolved in 90:10 (v/v) chloroform: methanol solution. The APTAC-PEI solution is then chilled to 0° C. in an ice bath. BBA-Cl (4-benzoylbenzoyl chloride) is then dissolved in chloroform and added to the chilled APTAC-PEI chloroform:methanol solution with stirring. The reaction is stirred overnight with gradual warming to room temperature. The reaction solution is then transferred into a large flask and one equivalent of concentrated hydrocholoric acid is added along with deionized water. The organic solvents are removed under vacuum at 40° C. until the aqueous BBA-APTAC-PEI solution is clear in appearance.

EXAMPLE 5

Preparation of APTAC-PEI Polymers of Various Molecular Weights

PEI polymers having $M_w$s of 750,000 (750K) Da, 10,000 (10K) Da, 2,000 (2K) Da, and 800 Da were obtained from Polysciences, Warrington, Pa. To prepare PEI having 50% APTAC coupling, a 2.4:1 w/w ratio of APTAC to PEI for each different sized PEI polymer was used. In to prepare PEI having 20% APTAC coupling, a 0.96:1 w/w ratio of APTAC to PEI for each different sized PEI polymer was used.

Reagents and reaction times as detailed in Example 3 were used for each of the preparations.

APTAC-PEI polymers of the recited sizes and having pendent BBA photoreactive groups are prepared using a synthetic scheme based on Example 4.

EXAMPLE 6

Trimethylolpropane Ethoxylate (20/3 EO/OH)

Triacrylate Macromer Preparation (Compound I)

A PEG-based macromer was synthesized as follows (synthesis scheme represented at the end of this Example).

Trimethylolpropane ethoxylate (PEG-triol; 100.0 g, 98.6 mmoles; Average Mw approximately 1,104; Cat. No. 41,617-7; Aldrich Chemical Company, Inc., Milwaukee, Wis.) was dissolved in 200 mls of toluene with stirring and refluxed for one hour. The PEG-triol solution was allowed to cool to approximately 80° C. At this time, 50 mg (0.403 mmoles) of 4-methoxyphenol (MEHQ; J. T. Baker, Phillipsburg, N.J.), 42.7 g (0.592 moles) of acrylic acid (J. T. Baker, Phillipsburg, N.J.), and 10 mls (0.188 moles) of sulfuric acid (Aldrich Chemical Company, Inc., Milwaukee, Wis.) were added with stirring to the reaction solution. The reaction solution was heated to reflux. The reaction was allowed to progress until about 6.0 mls of water was produced and collected via a Dean & Stark receiver (approximately one hour). The reaction mixture was allowed to cool to 50° C. and poured into a solution of sodium bicarbonate (270 g in 2.5 liters of deionized water) with stirring. The organic layer was separated, washed with deionized water and dried over sodium sulfate. The PEG-triacrylate was isolated using a wiped film still (Pope Scientific, Inc., Saukville, Wis.).

A PEG-triacrylate macromer product is represented by Compound I.

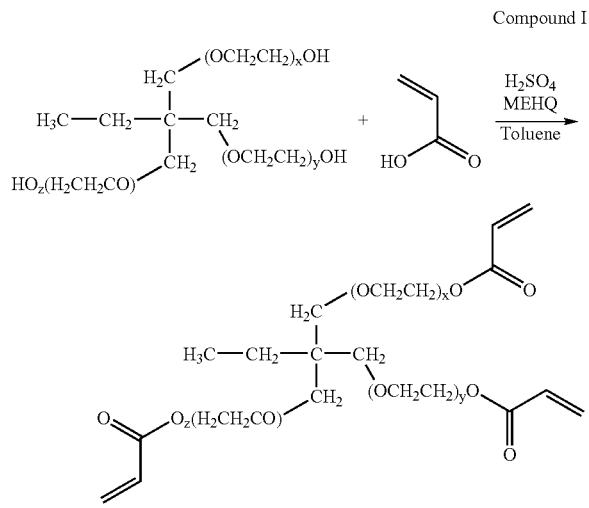

Compound I

EXAMPLE 7

Photo-Collagen Preparation

A photoreactive derivative of type IV collagen (photo-collagen) was prepared as follows. Human placental type IV collagen was obtained from Sigma Chemical Co., St. Louis, Mo. A heterobifunctional crosslinking agent (BBA-EAC-NOS) was synthesized and used to photoderivatize the collagen.

The BBA-EAC-NOS includes a benzophenone photoreactive group (BBA), a spacer (EAC) and an amine reactive thermochemical coupling group (N-oxysuccinimide, NOS). BBA-EAC was synthesized from 4-benzoylbenzoyl chloride and 6-aminocaproic acid. Then the NOS ester of BBA-EAC was synthesized by esterifying the carboxy group of BBA-EAC by carbodiimide activation with N-hydroxysuccinimide to yield BBA-EAC-NOS.

Type IV collagen was photoderivatized by covalently coupling primary amines on the protein via the NOS ester of BBA-EAC-NOS. The BBA-EAC-NOS was added at a ratio of 10-15 moles of BBA-EAC-NOS per mole of collagen.

EXAMPLE 8

4,5-bis(4-benzoylphenylmethyleneoxy) benzene-1,3-disulfonic acid disodium salt [DBDS] synthesis 4,5-bis(4-benzoylphenylmethyleneoxy) benzene-1,3-disulfonic acid disodium salt (DBDS) was prepared as follows. An amount (9.0 g, 0.027 moles) of 4,5-dihydroxy 1,3-benzene disulfonic acid disodium salt monohydrate was added to a 250 ml, 3 necked round bottom flask fitted with an overhead stirrer, gas inlet port, and reflux condenser. An amount (15 g, 0.054 moles) of 4-bromomethylbenzophenone (BMBP), 54 ml tetrahydrofuran (THF), and 42 ml deionized water were then added. The flask was heated with stirring under an argon atmosphere to reflux. The argon atmosphere was maintained during the entire time of refluxing.

After reflux was reached, 9.0 ml (6N, 0.054 moles) of a sodium hydroxide solution was added through the reflux condenser. The reaction was stirred under reflux for 3 hours. After this time, a second portion of BMBP, 3.76 g (0.014 moles), and 3.6 ml (6N, 0.022 moles) of sodium hydroxide were added. The reaction was continued under reflux for more than 12 hours, after the second BMBP addition.

The reaction mixture was evaporated at 40° C. under vacuum on a rotary evaporator to give 46 g of a yellow paste. The paste was extracted by suspending three times in 50 ml of chloroform at 40° C. for 30 minutes. A centrifuge was used to aid in the decanting of the chloroform from the solid. The solid was collected on a Buchner funnel, after the last extraction, and air dried for 30 minutes. The solid was then dried by using a rotary evaporator with a bath temperature of 50° C. at a pressure of about 1 mm for 30 minutes.

The dried solid, 26.8 g, was recrystallized from 67 ml of water and 67 ml of methanol. The dried purified product amounted to 10.4 g (theoretical yield was 19.0 g) with absorbance of 1.62 at 265 nm for a concentration of 0.036 mg/ml. See also U.S. Pat. No. 6,278,018.

EXAMPLE 9

Tetrakis (4-benzoylbenzyl ether) of Pentaerythritol ["tetra-BBE-PET"] Synthesis

The following were refluxed for 34 hours in an argon atmosphere: pentaerythritol [Aldrich] (2.0 g; 14.71 mmole, dried at 60° C. at <1 mm Hg for one hour); 4-bromomethylbenzophenone (20.0 g; 72.7 mmole; prepared by free radical bromination of 4-methylbenzophenone [Aldrich]); 80% (w/w) sodium hydride in mineral oil [Aldrich] (NaH, 1.23 g; 41.0 mmole); and tetrahydrofuran (THF, 120 ml).

An additional amount of 80% NaH (2.95 g; 98.3 mmole) was then added to the reaction mixture, and the mixture refluxed for an additional 7 hours under argon. The reaction was quenched by the addition of 8 ml of glacial acetic acid (HOAc). The quenched reaction was centrifuged to aid in the removal of THF insolubles.

The liquid was decanted, and the insolubles were washed with three 50 ml portions of chloroform ($CHCl_3$). The decanted liquid (mainly THF) and the $CHCl_3$ washes were combined and evaporated to give 18.7 g of a crude yellow semi-solid residue. A portion of the crude product (2 g) was purified by flash chromatography, using a 40 mm (1.58 inch) diameter by 200 mm (8 inch) long silica gel column eluted with $CHCl_3$ and diethyl ether ($Et_2O$) according to the following Table 2 (unless otherwise indicated, all ratios in the table are v/v):

TABLE 2

| Solvent (v/v) | Solvent volume (ml) | Fraction Numbers |
| --- | --- | --- |
| $CHCl_3$ - 100 | 500 | 01–22 |
| $CHCl_3/Et_2O$ - 98/2 | 500 | 23–46 |
| $CHCl_3/Et_2O$ - 95/5 | 1000 | 47–93 |
| $CHCl_3/Et_2O$ - 90/10 | 500 | 94–118 |

A light yellow oily product (0.843 g; 59% theoretical yield) was obtained by combining and evaporating fractions 81-105 (In theory, a yield of 1.43 g tetra-BBE-PET would be expected from 2.0 g of the crude product placed on the column). The purified light yellow product was confirmed by analysis using a Beckman Acculab 2 infrared spectrometer and a Varian FT-80 NMR spectrometer. The absence of a peak at 3500 cm-1 indicated the absence of hydroxyl functionality. Nuclear magnetic resonance analysis ($^1H$ NMR ($CDCl_3$)) was consistent with the desired product; aliphatic methylenes δ 3.6 (s, 8H), benzylic methylenes δ 4.5 (s, 8H), and aromatics δ 7.15-7.65 (m, 36H) versus tetramethylsilane internal standard.

The product is referred to as tetrakis (4-bezoylbenzyl ether) of pentaerythritol (tetra-BBE-PET).

EXAMPLE 10

PEG-Collagen Coatings

An ePTFE substrate is first primed with nonpolymeric initiator as follows. A coating solution of tetra-BBE-PET (prepared as described in Example 9) at a concentration of 0.5% v/v in IPA is prepared. The ePTFE substrate is then immersed in the coating solution of tetra-BBE-PET and illuminated in-solution for 3 minutes. Illumination is performed for 3 minutes midway between two opposed ELC-4000 lamps containing 400 watt metal halide/mercury vapor bulbs separated by a distance of 91 cm (36 inches). After a rinse with IPA to remove unbound tetra-BBE-PET, the substrate is allowed to dry. The resulting substrate contains a priming coating of tetra-BBE-PET.

After drying, the primed and dried substrate is dipped into a solution containing PEG-triacrylate macromer and tetra-BBE-PET in water (concentration PEG-triacrylate macromer is approximately 10-20% v/v, and tetra-BBE-PET is approximately 0.5-2% v/v). The substrate is withdrawn at a rate of 0.2 to 1.0 cm/s. The coated part is again illuminated, wet or dry, for 3 to 5 minutes (as described above).

The substrate is then dipped and subsequently withdrawn at a rate of 0.2 to 1.0 cm/s from a solution containing photo-collagen (prepared as described in Example 7) in IPA, at biocompatible agent concentrations of approximately 5-20% v/v. The substrate is again illuminated, wet or dry, for 3 to 5 minutes.

EXAMPLE 11 ePTFE Substrates Having PEG-Collagen Coatings

Coating solutions containing both polymeric matrix material and initiator in isopropyl alcohol (IPA) were prepared and applied to ePTFE substrates as follows. Sample conditions utilized for this experiment are summarized in Table 3. Coating solution compositions are shown in % volume for PEG-triacrylate macromer, and mg/ml for tetra-BBE-PET. Coating solutions for all samples were PEG-triacrylate macromer/tetra-BBE-PET in IPA. The soak time is the amount of time the substrates were immersed in the coating solution, and the UV time curing is the amount of time the substrate was illuminated with light to couple the coating to substrates.

TABLE 3

| Sample No. | Coating Solution (PEG-triacrylate macromer/tetra-BBE-PET) | Soak time (minutes) | UV Time Curing |
| --- | --- | --- | --- |
| 1 | 10% v/v/0.5 mg/ml | 10 | 3 |
| 2 | 10% v/v/0.5 mg/ml | 10 | 5 |
| 3 | 10% v/v/0.5 mg/ml | 20 | 3 |
| 4 | 10% v/v/0.5 mg/ml | 20 | 5 |
| 5 | 15% v/v/0.5 mg/ml | 10 | 3 |
| 6 | 15% v/v/0.5 mg/ml | 10 | 5 |
| 7 | 15% v/v/0.5 mg/ml | 20 | 3 |
| 8 | 15% v/v/0.5 mg/ml | 20 | 5 |

The ePTFE substrates were soaked in the coating solution, then illuminated wet for the indicated cure times by placing the substrate midway between two opposed ELC-4000 lamps containing 400 watt metal halide/mercury vapor bulbs separated by a distance of 91 cm (36 inches) in a UV chamber. The ePTFE substrates were saturated in the IPA coating solutions in an attempt to overcome hydrophobic nature of the material in order to couple a hydrophobic PEG-based coating on the surface.

Photoderivatized biocompatible agent was coupled to the substrates as follows. Photo-collagen, prepared as described in Example 7, was obtained in concentrations of 0.2 mg/ml in 12 mM HCl. The substrates were immersed in the photo-collagen solution, allowed to dwell in solution for 1 hour at 4° C., and then illuminated in-solution for 60 seconds per side utilizing a Dymax Blue Wave Spot Cure System (light system commercially available from Dymax Corporation, Torrington, Conn.). The ultraviolet wand of the system was placed at a distance to provide the substrate portions to be coated with approximately 0.5 to 0.25 $mW/cm^2$ of light in the wavelength range 330-340 nm. The substrates were gently agitated during the 60 seconds of illumination to ensure that the surfaces were evenly bathed in light.

The substrates were then removed from the photo-collagen solution. After removal of the substrates from the photo-collagen solution, the substrates were rinsed two times with sterile PBS for thirty minutes per wash, at a temperature of 4° C. The substrates were then soaked 30 minutes in 70% ethanol, then rinsed three times in sterile PBS (1 ml/wash). The substrates were stored in sterile PBS at 4° C.

EXAMPLE 12

Application of Collagen Macromer to PEBAX Substrates

A collagen macromer was prepared as follows. Bovine tendon collagen, Type I, was obtained from ReGen Corp. The collagen (0.5 grams) was dissolved in 20 ml dry formamide by incubating for 20 hours on an orbital shaker at 37° C. TEA was added with stirring, in an amount of 1.0 gram (9.8 mmole), and the reaction was equilibrated for 60 minutes in an ice water bath. Acryloyl chloride was added in 0.25 gram aliquots (rate of 1 aliquot per minute) with stirring, for a total amount of 1.0 gram (11 mmole) acryloyl chloride added. After the final addition, the solution was stirred in an ice water bath for 2 hours. The reaction was removed from the ice water bath and stirring was continued at room temperature for 18 hours. The product, collagen containing polymerizable groups (identified as "collagen macromer" in the Table 4 below), was purified by dialysis against deionized water using 6-8K MWCO dialysis tubing, and isolated by lyophilization.

PEBAX rods were obtained and subjected to coating with compositions summarized in the following Table 4.

TABLE 4

| Sample No. | Priming solution | Coating Composition |
| --- | --- | --- |
| 0 (control) | None | None |
| 1 | DBDS | Collagen macromer (20 mg/ml) |
| 2 | DBDS | Collagen macromer (20 mg/ml) |
| 3 | DBDS | Collagen macromer (30 mg/ml) |
| 4 | DBDS | Collagen macromer 30 mg/ml |
| 5 | DBDS | Collagen macromer 20 mg/ml; Photo-collagen (200 µg/ml) |
| 6 | DBDS | Collagen macromer 30 mg/ml; Photo-collagen (200 µg/ml) |

For all samples, priming was done by immersing the PEBAX substrates in a solution of DBDS in water at a concentration of 5 mg/ml. For all samples and coating steps in this Example, UV cure was performed by illuminating the substrates for 3 minutes in-solution, midway between two opposed ELC-4000 lamps containing 400 watt metal halide/mercury vapor bulbs separated by a distance of 91 cm (36 inches). Samples were rinsed to remove unbound Compound IV.

Next, samples were dipped in solutions of collagen macromer at the concentrations identified in Table 4 in water. Coating rates were as follows: 0.75 cm/s for Samples 1-3 and 5-6; 1.0 cm/s for Sample 4. Following the collagen macromer coating step, the Samples 2-6 were illuminated, wet, for 5 minutes. Sample 1 was allowed to air dry subsequent to the collagen macromer coating step, then illuminated dry for 3 minutes.

Samples 5 and 6 were then subjected to an additional coating of photo-collagen (prepared as described in Example 7) as follows. Solutions of photo-collagen at concentration of 200 µg/ml in water were prepared. Substrates were dipped into the photo-collagen solutions at a rate of 0.75 cm/s. The substrates were then illuminated, wet, for 5 minutes.

Completed samples were subject to FITC staining to determine coating efficacy. For FITC staining, 10 mg FITC (Isomer I, Molecular Probes F-1906) was solubilized in 2 ml of 100% ethanol. The solubilized FITC was stored at −20° C. until use (concentration=5 mg/ml). Upon use, the FITC was diluted 1:20 in 0.1 M borate buffer, pH 9.0 to 250 µg/ml. Samples were immersed in the FITC stain for 1 hour in the dark at room temperature. After staining, the samples were removed from the stain, rinsed four times with borate buffer, followed by a rinse with water, then air dried. Samples were observed by fluroescent microscopy.

Results indicated that all coated samples stained strongly and appeared uniform and consistent from one sample to the next. Subsequent contrast enhancement revealed minor inconsistencies in several of the coatings. Coating 2, with collagen macromer at 20 mg/ml illuminated wet for 5 minutes, appeared to stain less intensely than macromer coatings illuminated dry, at higher concentrations, and/or with an additional topcoat of photo-collagen.

EXAMPLE 13

Application of Collagen Macromer to Silicone and Titanium Substrates

Silicone and titanium were coated with a first coating solution prepared from a combination of 20 mg/mL PVP K90 (International Specialty Products, Wayne, N.J.), 15 mg/mL photo-derivatized poly(vinylpyrrolidone) (photo-PVP) as prepared as described in U.S. Pat. No. 5,637,460, 0.5 mg/mL tetra-BBE-PET, and 1 mg/mL DBDS in a 60% IPA/40% water mixture. Substrates were dip-coated in this solution at a rate of 0.20 cm/s, air dried for 10 minutes or greater, and then subject to UV irradiation for 3 minutes.

The substrate with this first coated layer was then dip coated in a solution of 10% (v/v) PEG macromer, 0.7% mg/mL tetramethylethylenediamine-diMBP-quat. (TEMED-DQ) (commercially available from SurModics, Eden Prairie, Minn.) in water at a rate of 0.75 cm/s and in solution illuminated with UV for 3 minutes.

The substrate with first and second coated layers was then dip coated in a solution of 10% collagen macromer, 0.8% mg/mL Tetramethylethylenediamine-diMBP-quat. (TEMED-DQ) in water at a rate of 0.75 cm/s and in solution illuminated with UV for 3 minutes.

The collagen macromer coating had improved lubricity over coatings that had a PEG outer layer, or a PEG/heparin outer layer. In addition FTIC analysis showed the coating was well formed before and after durability testing wherein the sample was wiped 20× with a cloth wipe with either saline or IPA.

EXAMPLE 14

Application and Analysis of Collagen Macromer Coatings on Polyurethane Substrates Various samples were prepared to optimize coating formulation(s) for PEG macromer/photoinitiator (TEMED-DQ)/collagen macromer and collagen macromer/photoinitiator (TEMED-DQ) dip coatings, on a polyurethane substrate. After coatings were performed surface analysis was conducted by imaging collagen macromer coatings, including staining with Fast Green dye and FITC analysis. All samples were treated with a base coat of photo-PVP/tetra-BBE-PET (10/0.5 mg/ml in IPA, lift rate 0.10 cm/s, air dry, UV 3 min.) prior to the coating work detailed below. All other coating solutions were aqueous. Subscripts (i.e. 1a, 1b) indicate multiple coating layers on the same sample, intended to represent a two-step coating process.

TABLE 5

| Sample # | Lift rate (cm/s) | PEG macromer % v/v | photoinitiator (TEMED-DQ) mg/ml | Collagen Macromer mg/ml | UV (min.) |
|---|---|---|---|---|---|
| 1a | 0.50 | 5 | 0.5 | — | 3 |
| 1b | 0.50 | — | 0.8 | 10 | 3 |
| 2a | 0.50 | 5 | 0.5 | — | 3 |
| 2b | 0.50 | — | 0.8 | 15 | 3 |
| 3a | 0.50 | 10 | 0.7 | — | 3 |
| 3b | 0.50 | — | 0.8 | 10 | 3 |
| 4a | 0.50 | 10 | 0.7 | — | 3 |
| 4b | 0.50 | — | 0.8 | 15 | 3 |
| 5 | 0.50 | 5 | 0.5 | 5 | 3 |
| 6 | 0.50 | 10 | 0.5 | 5 | 3 |
| 7 | 0.50 | 5 | 0.5 | 15 | 3 |
| 8 | 0.50 | — | 10 | 0.8 | 1 |
| 9 | 0.50 | — | 15 | 0.8 | 2 |
| 10 (2× dip) | 0.50 | — | 15 | 0.8 | 4 |

Prior to coating, all samples were sonicated for 30 minutes in IPA to clean the surface of the substrate. Following sonication, the samples were wiped with an IPA-saturated cloth and allowed to air dry.

A small area at the top of each sample, where the sample was suspended with an alligator clip, was uncoated; the majority of the sample surface was covered with base layer and with PEG macromer/TEMED-DQ photoinitiator (for samples which received a separate PEG macromer/TEMED-DQ photoinitiator layer); then approximately half of the sample was dipped into the collagen macromer solution (either collagen macromer TEMED-DQ or PEG macromer/TEMED-DQ/collagen macromer as listed above).

After coating, all samples were stained with Fast Green (a food dye, at 0.5% w/w in water, approx. one minute of stain immersion) and duplicate samples were also stained by FITC.

FITC samples were processed as follows: 10 mg FITC dye was dissolved in 2 ml ethanol, then diluted 1:20 in 0.1 M borate buffer (pH ~9.0) to a final concentration of 250 µg/ml. Samples were immersed in FITC stain for 1 hour protected from light. Samples were rinsed 4× with borate buffer, and observed by fluorescent microscopy; images were captured.

In addition to the samples listed in the matrix above, one uncoated control and one sample with a base layer (photo-PVP/tetra-BBE-PET) only were included in the FITC assay. The sample with a base layer only did produce some background fluorescence; the offset on the microscope was adjusted to account for this effect, and images were captured after this adjustment.

For both PEG macromer/TEMED-DQ/Collagen Macromer and PEG macromer/TEMED-DQ+collagen macromer/TEMED-DQ formulations, using a higher level of PEG macromer (10% v/v) appears to produce a coating which is more even and uniformly thick.

What is claimed is:

1. An implantable medical article comprising a pro-fibrotic coating, the pro-fibrotic coating comprising (a) collagen, (b) thromboresistant agent, and (c) a reacted photogroup, wherein the coating comprises a first coated layer comprising free-radically polymerized thromboresistant agent that is positioned between a second coated layer comprising the collagen and a surface of the article, and the coating is formed by applying the collagen and thromboresistant agent independently to the article.

2. The implantable medical article of claim 1 wherein the coating is formed from a composition comprising collagen comprising a pendent photoreactive group.

3. The implantable medical article of claim 1 wherein the reacted photogroup bonds collagen to the thromboresistant agent.

4. The implantable medical article of claim 1 wherein the collagen comprises collagen type I.

5. The implantable medical article of claim 1 wherein the coating is formed from a composition comprising a compound comprising a photoreactive group, collagen, and a thromboresistant agent, and the compound comprising the photoreactive group is independent of the collagen or the thromboresistant agent.

6. The implantable medical article of claim 5 wherein the first coated layer is formed from a composition comprising a free-radically polymerizable thromboresistant agent and a polymerization initiator.

7. The implantable medical article of claim 5 wherein the compound comprises two or more photoreactive groups.

8. The implantable medical article of claim 6 wherein the collagen comprises a pendent polymerized group.

9. The implantable medical article of claim 8 comprising a layer of polymerized collagen.

10. The implantable medical article of claim 1 wherein the thromboresistant agent comprises a polymer.

11. The implantable medical article of claim 1 wherein the thromboresistant agent is present in the coating in an amount of 10% (wt) or greater.

12. The implantable medical article of claim 10 wherein the thromboresistant polymer comprises poly(ethylene glycol).

13. The implantable medical article of claim 1 wherein the pro-fibrotic coating is less than 5 µm in thickness.

14. The implantable medical article of claim 1 comprising a vascular occlusion device.

15. The implantable medical article of claim 1 comprising a cardiac patch.

16. The implantable medical article of claim 12 wherein a portion of the coating is formed from a composition comprising poly(ethylene glycol)-triacrylate macromer.

17. The implantable medical article of claim 1 wherein the coating is formed from a first composition comprising the thromboresistant agent a concentration in the range of 10-20% wt, and a second composition comprising the collagen at a concentration in the range of 5-20% wt.

18. The implantable medical article of claim 1 comprising a priming layer located between the first layer and the surface of the device, the priming layer comprising the reacted photogroup.

19. The implantable medical article of claim 1 wherein the free-radically polymerized thromboresistant agent comprises a free radically polymerized group selected from the group consisting of vinyl groups, acrylate groups, methacrylate groups, ethacrylate groups, 2-phenyl acrylate groups, acrylamide groups, methacrylamide groups, itaconate groups, and styrene groups.

20. The implantable medical article of claim 1 which is formed from material selected from the group consisting of poly(urethanes), poly(acrylates), poly(methacrylates), poly(vinylpyrrolidone), cellulose acetate, ethylene vinyl alcohol copolymers, poly(acrylonitrile), poly(vinylacetate), cellulose acetate butyrate, nitrocellulose, copolymers of urethane/carbonate, and copolymers of styrene/maleic acid.

21. The implantable medical article of claim 1 which is formed from material selected from the group consisting of platinum, gold, tungsten, rhenium, palladium, rhodium, ruthenium, titanium, nickel, stainless steel, titanium/nickel alloy, and nitinol alloy.

* * * * *